United States Patent [19]
Fellman

[11] 3,993,888
[45] Nov. 23, 1976

[54] SCANNING LINE FILTER
[75] Inventor: Daniel J. Fellman, Williamsville, N.Y.
[73] Assignee: Calspan Corporation, Buffalo, N.Y.
[22] Filed: Oct. 29, 1974
[21] Appl. No.: 518,442

[52] U.S. Cl. .............................. 235/151; 250/211 J; 250/209; 340/146.3 E; 340/146.3 F
[51] Int. Cl.[2] ......................................... H01L 31/08
[58] Field of Search ............... 340/146.3 E, 146.3 F; 250/211 J; 356/71; 235/151

[56] References Cited
UNITED STATES PATENTS

| | | | |
|---|---|---|---|
| 3,688,166 | 8/1972 | Desvignes | 357/32 |
| 3,689,772 | 9/1972 | George et al. | 250/211 J |
| 3,770,940 | 11/1973 | Harr | 340/146.3 H |
| 3,788,749 | 1/1974 | George | 356/71 |

Primary Examiner—Eugene G. Botz
Attorney, Agent, or Firm—Allen J. Jaffe

[57] ABSTRACT

An image processing device for enhancing and digitizing images made up primarily of continuous parallel lines such as contour maps and fingerprints. An image is focused on a photodiode detector array and a digital logic signal is produced which is the binary representation of the portion of the image centered on the array.

7 Claims, 6 Drawing Figures

SCANNING LINE FILTER

Fingerprint images present problems in enhancement and digitization since they are subject to a number of conditions which produce image degradation. The physical sources of distortion include: dirt; scars; cuts and/or skin surface abrasions; skin oil and/or perspiration; plastic deformation of the skin; warts; print smearing; over-inking; and, under-inking. Contour maps also can contain a number of sources of discontinuities and extraneous/non-contour lines which include: elevation markings; political division markings; geological markings; longitude and latitude markings; and, labeling.

It is an object of this invention to provide a device for enhancing and digitizing images made up primarily of continuous parallel lines.

It is a further object of this invention to provide a line-following device suitable for following the contour lines on a topographic map.

It is an additional object of this invention to provide a device for enhancing and digitizing an optical image in a terminal for the direct reading of fingerprints. These objects, and others as will become apparent hereinafter, are accomplished by the present invention.

Basically, the present invention is directed to a device for enhancing and digitizing images made up primarily of continuous lines, which, over short distances are generally parallel lines. According to one embodiment, a scan of small portions of the image is taken and the image is processed and digitized. According to a second embodiment, a continuous line is followed by determining the direction of the line in the portion of the image being scanned.

BRIEF DESCRIPTION OF THE DRAWINGS

For a fuller understanding of the present invention, reference should now be had to the following detailed description thereof taken in conjunction with the accompanying drawings wherein.

DESCRIPTION OF THE PREFERRED EMBODIMENT

Figure 1:
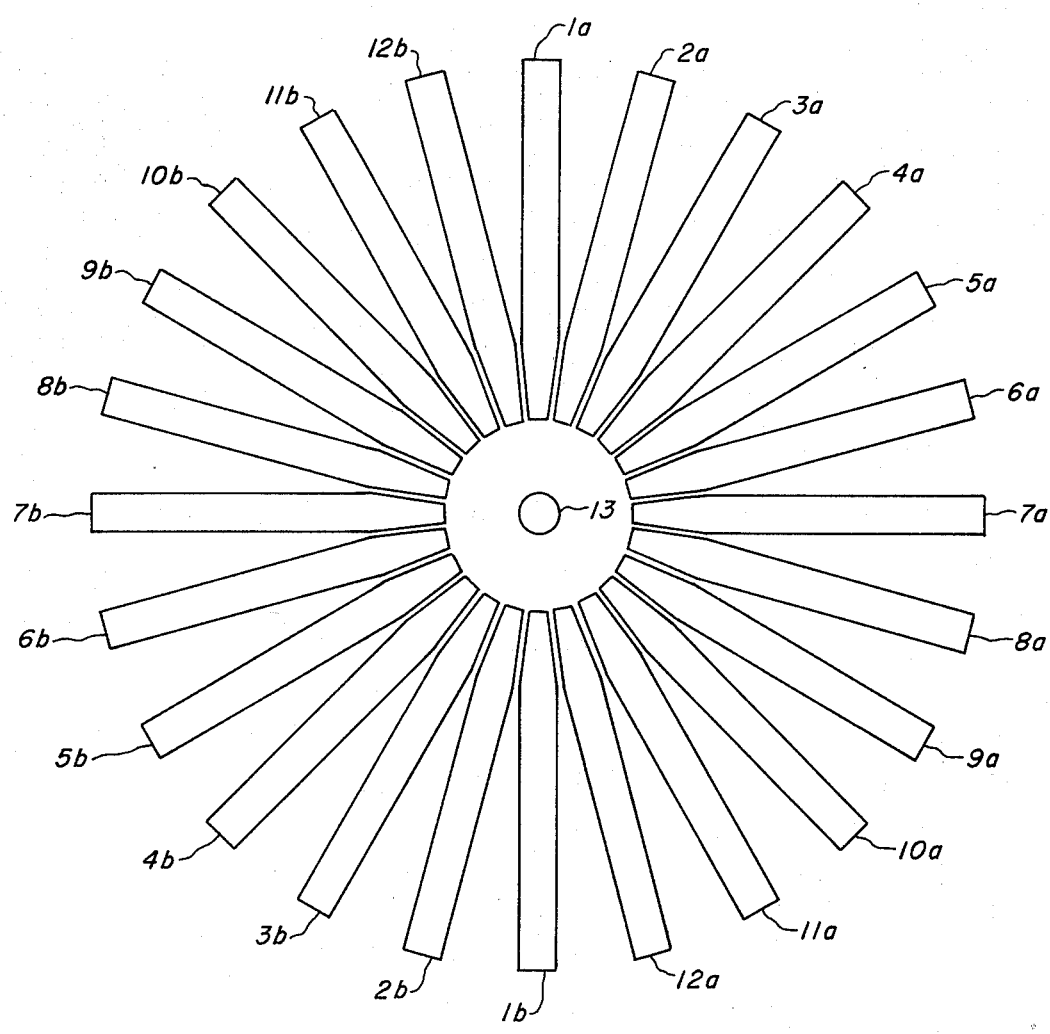
FIG. 1 is a view of the photodiode detector array.
Figure 2:
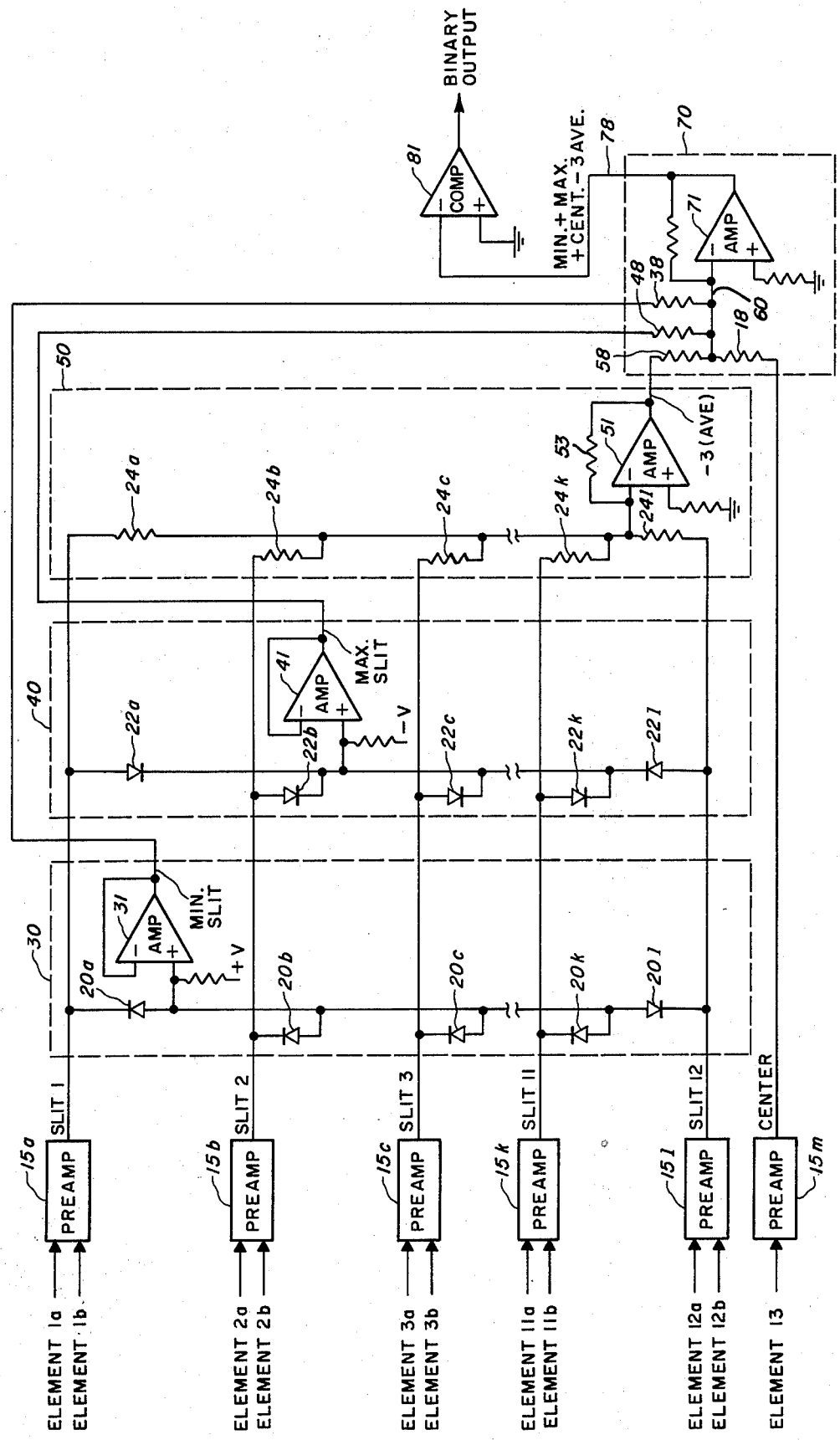
FIG. 2 is a schematic diagram of the line filter circuits.

The photodiode detector array of FIG. 1 consists of a circular central element surrounded by twenty-four radial elements. Each diametrically located pair of radial elements constitutes a slit. Slit 1 consists of radial elements 1a and 1b and slits 2–12 are similarly numbered. Central element 13 as well as each of the radial elements of slits 1–12 are electrically connected to provide the inputs to preamplifiers 15a–m of FIG. 2. The outputs of slits 1–12 and central element 13 are currents which are proportional to the incident light and these currents are converted to voltages with a gain by preamplifiers 15a–l and are communicated to a minimum detector diode tree consisting of diodes 20a–l through which the output of the slit having the least incident light is communicated to the positive input of buffer amplifier 31 of minimum detector circuit 30. The outputs of slits 1–12, respectively, are communicated to a maximum detector diode tree consisting of diodes 22a–l and the output of the slit having the most incident light is communicated to the positive input of buffer amplifier 41 of maximum detector circuit 40. Similarly, the outputs of slits 1–12, respectively, are communicated to a slit averaging resistor tree consisting of resistors 24a–l and the resulting output which is the average output of slits 1–12 is communicated to the negative input of amplifier 51 of slit averaging circuit 50. The ratios of the resistors 24a–l and resistor 53 are such as to give a gain of three in slit averaging circuit 50. The output of minimum detector circuit 30, which is the output of the slit having the minimum output, is communicated to line 60 via resistor 38 of summing circuit 70. The output of maximum detector circuit 40, which is the output of the slit having the maximum output, is communicated to line 60 via resistor 48 of summing circuit 70. The output of slit averaging circuit 50, which is minus three times the average output of slits 1–12, is communicated to line 60 via resistor 58 of summing circuit 70. The output of preamplifier 15m, which is the output of central element 13, is communicated to line 60 via resistor 18 of summing circuit 70. The outputs of circuits 30, 40 and 50 and preamplifier 15m which are communicated to line 60 together make up the negative input to amplifier 71 of summing circuit 70. The output of summing amplifier circuit 70, which is the sum of the outputs of the minimum and maximum slits plus that of the central element 13 minus three times the average slit output, is communicated via line 78 to the negative input of comparator 81. The output of comparator 81 is a digital logic signal which is the binary representation of the output of the photodiode detector array.

OPERATION

Figure 3:
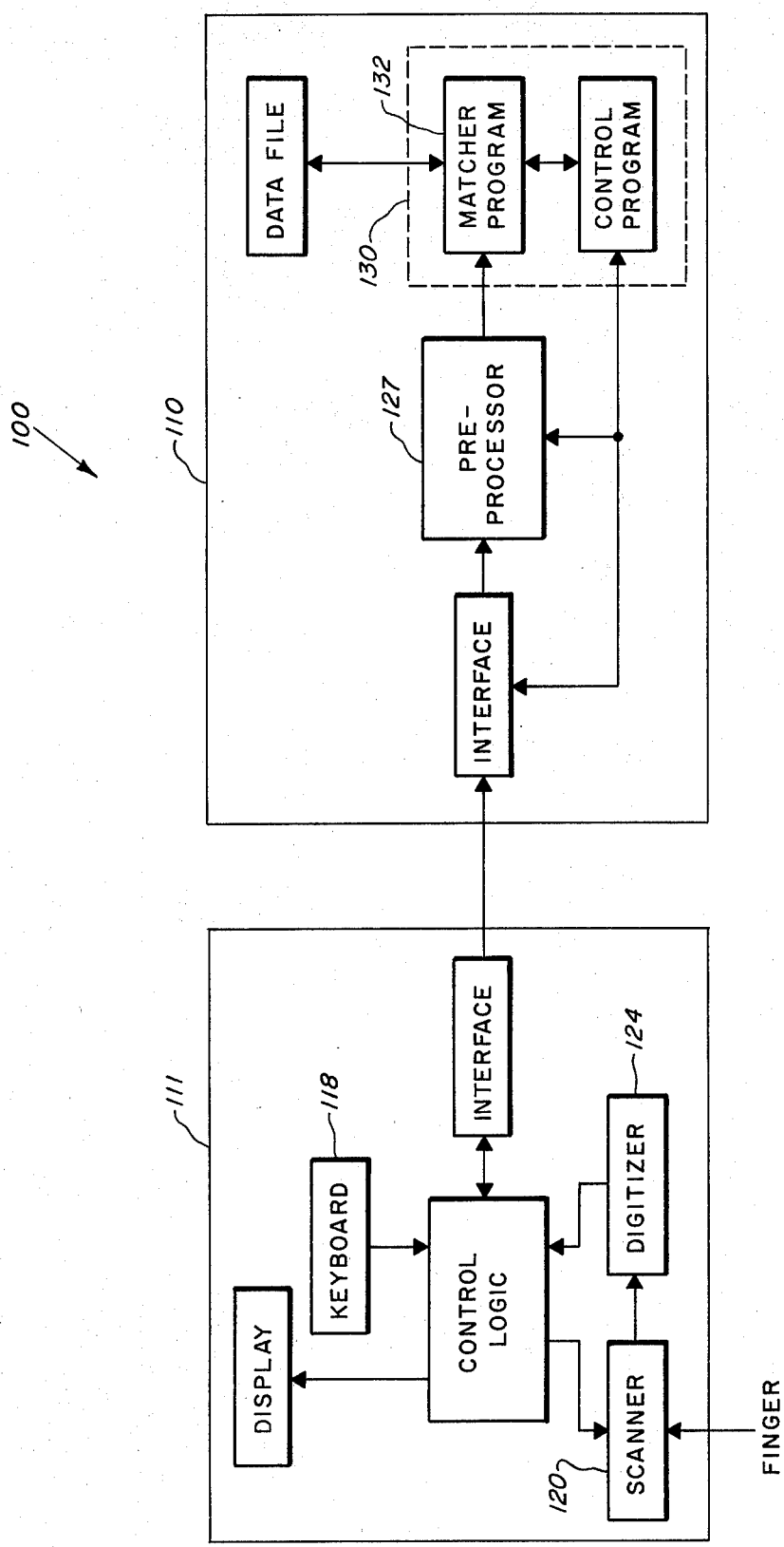
FIG. 3 is a block diagram of a fingerprint identification system employing the device of FIGS. 1 and 2.
Figure 5:
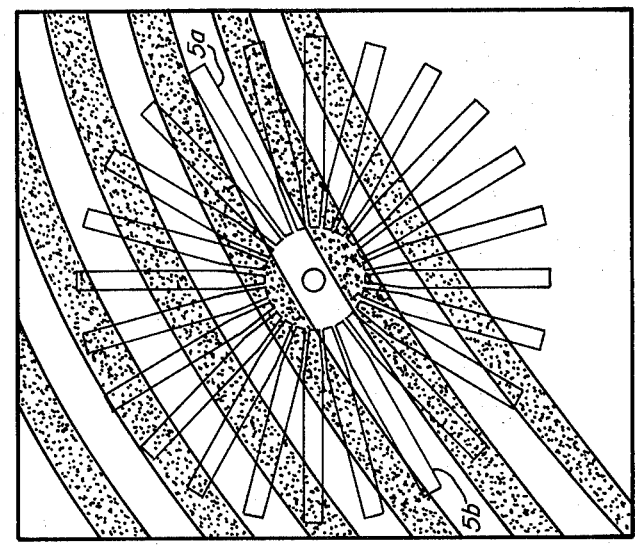
Figure 4:
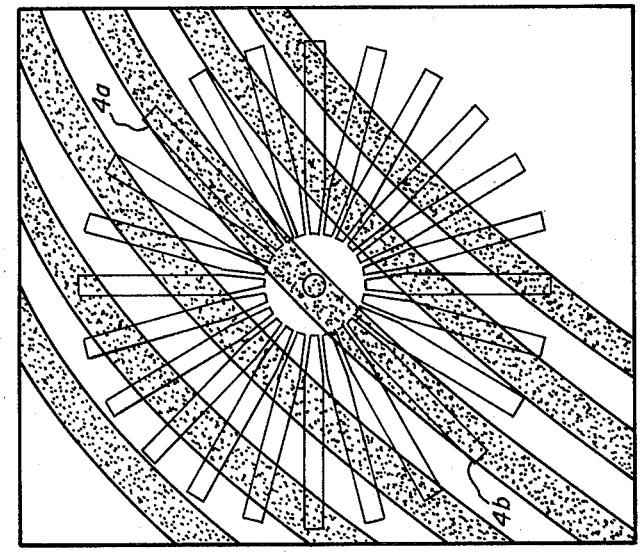

In FIG. 3 the numeral 100 generally designates a fingerprint based identification system which includes a central system 110 and one or more terminals 111. Each terminal 111 includes a keyboard 118 on which the person to be identified keys in an identification number and this number is sent to central system 110. The person to be identified places his finger against a clear optical glass prism which is a part of scanner 120. When a finger is placed against an illuminated prism face, the result is a change in the internal reflection of light in a pattern which corresponds to that of the fingerprint. The light pattern of the fingerprint is magnified and focused on the photodiode detector array of FIG. 1 which forms a part of digitizer 124 and in this application would have a typical diameter of 0.15 inches. As best seen in FIGS. 4 and 5, the pattern of the fingerprint wherein the ridges of the fingerprints correspond to the shadowed areas, represented by stippling, is focused on the photodiode detector array. A directional filtering effect is provided by the line filter circuits of FIG. 2. If the image contains a line that passes through the central element 13 of the array, in general that line will lie largely along one of the slits, slit 4 of FIG. 4. Or, if the central element 13 falls between lines, in general, one of the slits will also lie largely between lines, slit 5 of FIG. 5. However, given that the other lines in the image are mostly parallel, they will lie mostly across the remaining slits. The important point is that in either case the aligned slit output will deviate from the average slit value while the outputs of the other slits approach it.

Basically, the digitizer 124 is a local light averager, i.e., the output of the central element 13 is compared with the average output of the twelve opposing element pairs making up slits 1–12. Depending upon whether the center output is smaller (darker) or larger (lighter) than the average, the image at the point is digitized as either 1 or 0. However, the comparison is biased by the minimum and maximum slit values, which contain directional filtering information.

The local averaging and directional filtering are combined by evaluating the inequality.

$$\text{center} + \text{minimum} + \text{maximum} < 3 \times \text{average}.$$

If it holds, the image point is declared black; if not, white. If a line runs through the central element 13, as in FIG. 4, the minimum will be further below the average than the maximum is above it and the expression is biased toward the black. Conversely, if the central element 13 falls between lines, as in FIG. 5, the maximum will be further above the average than the minimum is below it and the expression is biased toward the white. The result is that small breaks or light areas in the line structure are "filled in" and spots and smudges in the spaces are eliminated.

By virtue of its shape, the photodiode detector array greatly simplifies the implementation of this algorithm. Previous realizations in software or digital hardware employed what are essentially point photodetectors. It was necessary to pre-digitize the image and store grey scale values for sections of it in some form of memory, then retrieve and combine appropriate values to form the slits. This was time-consuming in the software and expensive in the hardware. But with the special detector, outputs for all the slits are immediately and simultaneously available and because they are still in analog form it is easy to evaluate minimum, maximum, and average values and to perform the weighted comparison that produces the binary output of comparator 81.

The real image of the fingerprint is moved across the photodiode detector array in a raster scan to thereby sample and obtain the corresponding binary image. The identification number keyed in on keyboard 118 and the digitized print from digitizer 124 are sent to the central system 110 where a hardware preprocessor 127 locates minutiae. The minutiae coordinates are then sent to a computer 130 where a matcher program 132 compares them with those on file for the person, verifying or not verifying his identity.

Figure 6:
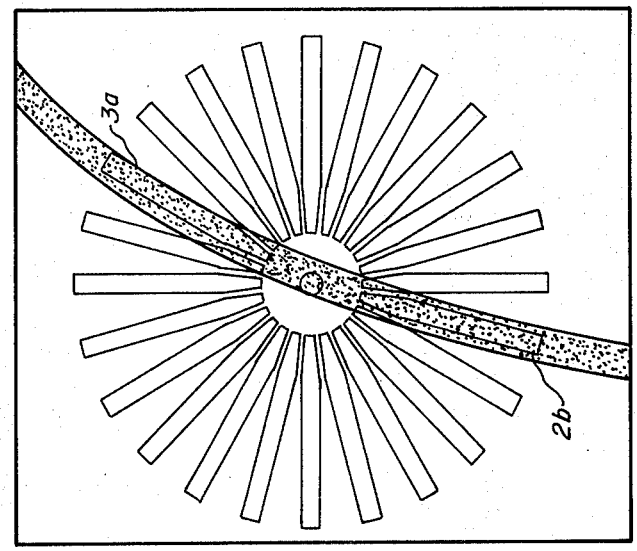
FIGS. 4, 5 and 6 show a magnified image superimposed upon the photodiode detector array of FIG. 1.

Although the invention has been described in terms of a device for the direct reading of fingerprints, it is also applicable to the reading of inked fingerprints and for line-following applications. In line-following applications the slit providing the extreme value must be identified by the maximum or minimum detector circuits. Where, as illustrated in FIG. 6, a single curved line is being detected, the line may not be aligned with a single slit and there may be more than one slit having an extreme value. In the illustrated example, a non-diametrically located slit defined by elements 3a and 2b would have a more extreme reading than any slit containing diametrically located pairs of elements. It therefore becomes desirable to provide alternate pairings of elements to define a slit as by testing elements on either side of one of the diametrically located elements having an extreme value. In the example of FIG. 6, element 3a would be sequentially paired with elements 3b, 2b and 4b and element 2a would be paired with elements 2b, 1b and 3b since slits 2 and 3 would have the extreme readings of the diametrically located element defining slits. Similarly elements 3a, 2a and 4a may be paired with element 3b and elements 2a, 1a and 3a may be paired with element 2b. In this manner the slit defined by elements 3a and 2b can be determined to have the most extreme reading and therefore would define the locus of the line.

Although a preferred embodiment of the present invention has been illustrated and described, other changes will occur to those skilled in the art. For example, the gain in the slit averaging circuit can be changed, the number and dimension of the slits in the photodiode detector array may be changed as may the magnification of the image focused thereon and the outputs of the elements may be either linear or nonlinear. It is therefore intended that the scope of the present invention is to be limited only by the scope of the appended claims.

I claim:
1. An image processing means for enhancing and digitizing images including:
   photodiode detector array means defined by a plurality of pairs of diametrically located, radially extending pairs of elements surrounding a central element with each of said elements producing a current output proportional to light incident thereon;
   a plurality of preamplifier means for converting the current outputs of each of said pairs of elements and said central element into voltages which are supplied as output signals;
   minimum detector means connected to each of said preamplifier means for said pairs of elements and which produces an output signal representative of the least incident light on a pair of said pairs of elements;
   maximum detector means connected to each of said preamplifier means for said pairs of elements and which produces an output signal representative of the most incident light on a pair of said pairs of elements;
   averaging means connected to each of said preamplifier means for said pairs of elements and which produces an output signal equal to the average value of all of said pairs of elements with a predetermined gain;
   summing means for summing the output signals from said minimum detector means, said maximum detector means, said averaging means and said preamplifier means connected to said central element for producing an output signal which is representative of the sum of the signals supplied thereto; and
   comparator means connected to said summing means and producing a digital logic signal which is the binary representation of the output of said elements of said photodiode detector array means.

2. The image processing means of claim 1 wherein said minimum detector means includes buffer amplifier means and diode tree means, said diode tree means being interposed between said preamplifier means for said pairs of elements and said buffer amplifier means which furnishes said output signal representative of the least incident light on a pair of said pairs of elements.

3. The image processing means of claim 1 wherein said maximum detector means includes buffer amplifier means and diode tree means, said diode tree means being interposed between said preamplifier means, said diode tree means being interposed between said preamplifier means for said pairs of elements and said buffer amplifier means which furnishes said output signal representative of the most incident light on a pair of said pairs of elements.

4. The image processing means of claim 1 wherein said averaging means includes first amplifier means and resistor tree means, said resistor tree means being interposed between said preamplifier means for said pairs of elements and said first amplifier means which furnishes said output signal representative of the average value of all of said pairs of elements.

5. The image processing means of claim 4 wherein said minimum detector means includes first buffer amplifier means and diode tree means, said diode tree means being interposed between said preamplifier means for said pairs of elements and said first buffer amplifier means which furnishes said output signal representative of the least incident light on a pair of said pairs of elements.

6. The image processing means of claim 5 wherein said maximum detector means includes second buffer amplifier means and diode tree means, said diode tree means being interposed between said preamplifier means for said pairs of elements and said second buffer amplifier means which furnishes said output signal representative of the most incident light on a pair of said pairs of elements.

7. The image processing means of claim 4 wherein said predetermined gain of said averaging means is minus three.

* * * * *

UNITED STATES PATENT OFFICE
CERTIFICATE OF CORRECTION

PATENT NO. : 3,993,888
DATED : November 23, 1976
INVENTOR(S) : Daniel J. Fellman It is certified that error appears in the above-identified patent and that said Letters Patent are hereby corrected as shown below:

In claim 3 at lines 4-6 cancel ", said diode tree means being interposed between said preamplifier means".

Signed and Sealed this

Eighth Day of March 1977

[SEAL]

Attest:

RUTH C. MASON
Attesting Officer

C. MARSHALL DANN
Commissioner of Patents and Trademarks